United States Patent [19]

Leuba

[11] 4,094,743

[45] June 13, 1978

[54] ENZYMES IMMOBILIZED ON CHITOSAN

[75] Inventor: Jean-Louis Leuba, Crissier, Switzerland

[73] Assignee: Societe d'Assistance Technique pour Produits Nestle S.A., La Tour-de-Peilz, Switzerland

[21] Appl. No.: 672,790

[22] Filed: Apr. 1, 1976

[30] Foreign Application Priority Data

Apr. 10, 1975 Switzerland .......................... 4546/75

[51] Int. Cl.$^2$ ................................................ C07G 7/02
[52] U.S. Cl. ......................................... 195/63; 195/68; 195/DIG. 11
[58] Field of Search ................... 195/63, 68, DIG. 11; 260/112

[56] References Cited

U.S. PATENT DOCUMENTS

| | | |
|---|---|---|
| 3,368,940 | 2/1968 | Turner, Jr. et al. ............. 260/112 T |
| 3,539,450 | 11/1970 | Deutsch ................................. 195/68 |
| 3,706,633 | 12/1972 | Katchalski et al. .................... 195/63 |
| 3,883,394 | 5/1975 | Savidge et al. ......................... 195/63 |
| 3,909,358 | 9/1975 | Stanley et al. ......................... 195/63 |

*Primary Examiner*—David M. Naff
*Attorney, Agent, or Firm*—Watson, Leavenworth, Kelton & Taggart

[57] ABSTRACT

An enzymatically active product insoluble in aqueous medium is prepared by treating chitosan as an inert support with a dialdehyde, after which an enzyme is fixed to the support thus treated. The chitosan may be in powder-form or in flake-form, for example obtained by fragmenting a film of anhydrous chitosan. The enzymatically active product insoluble in aqueous medium may be treated with a compound containing an amino group and/or with a reducing reagent. The product may be freeze dried optionally in the presence of twice its weight of mannitol.

18 Claims, No Drawings

ENZYMES IMMOBILIZED ON CHITOSAN

This invention relates to a process for the preparation of an enzymatically active product insoluble in aqueous medium.

The increasingly more frequent performance and utilisation of enzymatic reactions have shown the numerous advantages of enzymatically active products insoluble in aqueous medium. Firstly, these products enable the stability of the enzyme under the working conditions envisaged to be improved, secondly they enable the enzyme to be readily isolated from the substance to be treated (which is generally called the substrate) which means in particular that an enzymatic reaction can be stopped by simple mechanical separation of the "insoluble" enzyme and the substrate without any need for the enzyme to be inactivated by heating and without contaminating the substrate.

It has proved to be particularly interesting to fix an enzyme to an inert support. Thus, numerous processes for fixing enzymes to supports have been proposed, including in particular the adsorption of an enzyme onto an insoluble support or fixing the enzyme to the support by means of a bifunctional reactant.

The products obtained by the adsorption of an enzyme onto an insoluble support have the disadvantage of being substantially unstable because the cohesion of the combination is based on electrostatic forces. On the other hand, the products obtained by fixing an enzyme to a support by means of a bifunctional reactant are more stable because the cohesion of the combination is due to the presence of co-valent bonds. The support is normally formed by such materials as ceramics, glass, silica etc., and the bifunctional reactant is present in the end product in polymerised form. In other words, the end product is formed by an inert support surrounded by a shell of a polymer to which the enzyme is fixed.

In general, products such as these are not distinguished by particularly outstanding enzymatic activity in contrast to the enzymatically active product insoluble in aqueous medium obtained by the process according to the present invention.

The present invention provides a process for the preparation of an enzymatically active product insoluble in aqueous medium, in which chitosan as an inert support is treated with a dialdehyde, after which an enzyme is fixed to the support thus treated.

The invention also relates to the product obtained by this process. The product according to the invention may be used in enzymatic reactions instead of the corresponding enzyme in soluble form and may either be recovered on completion of the reaction by mechanical separation or may be used as a material for filling columns through which the substrate is passed.

Chitosan is a natural polymer obtained by the deacetylation of chitin in a strongly basic medium at elevated temperature. It is insoluble in water unless a dilute acid other than sulphuric acid is present.

Chitin is the main organic constituent of the protective envelope of the invertebrata (shells of crustations or cuticles of insects) which is also found in the skeletal wall of certain lower vegetable forms (mushrooms for example). It is a linear polymer of N-acetal-D-glucosamine of high molecular weight (approximately 200,000) which is characterised by bonds of the type $\beta(1\rightarrow 4)$. Since the N-acetal group is difficult to eliminate, deacetylation is never complete and generally varies from 50 to 85% in commercial products. It is these products which are known by the name of chitosan.

The bifunctional reactant selected from dialdehydes may be, for example, a dialdehyde with a chain of 1 to 10 carbon atoms, advantageously 3 to 6 carbon atoms, more especially malonaldehyde, succinaldehyde, glutaraldehyde, adipaldehyde. It is normally preferred to use glutaraldehyde which has the advantage of being an inexpensive commercial product and which gives products with remarkable enzymatic activity.

Fixing of the enzyme is carried out in two stages. In a first stage, the so-called "activation" stage, chitosan is treated with the bifunctional reactant selected from dialdehydes, for example glutaraldehyde. The dialdehyde is fixed to the chitosan through one of its aldehyde groups, and an intermediate product is obtained, namely a "activated chitosan", whose surface is covered with aldehyde groups. In a second stage, the enzyme is fixed to the activated chitosan. These operations are carried out very simply by contact, for example by immersion of the solid phase in the liquid phase under the following conditions:

treatment of the chitosan solution of the dialdehyde with a PH value of from 6 to 8, preferably a buffer solution, temperature from 2° to 35° C, preferably ambient temperature, treatment time from 30 minutes to 24 hours, preferably treatment in the absence of air and elimination of the excess dialdehyde by washing with water.

fixing of the enzyme suspension of the activated chitosan in a solution with a pH-value of from 2 to 11, preferably a buffer solution of pH 8.0 and containing $CaCl_2$ in a concentration of 0.02M, addition of the enzyme in solution in an aqueous medium, temperature from 2° C to the temperature at which the enzyme is inactivated, preferably around 2° C, treatment time from 2 to 24 hours, elimination of the unfixed enzyme by washing with a saline solution, the buffer solution used for fixing, and then with water.

Accordingly, the process according to the invention is applicable to enzymes containing functional groups capable of reacting with the free aldehyde groups in the activated chitosan, for example the free amino groups of certain amino acids, such as lysine.

The physical nature of the chitosan used does not have any significant effect upon the enzyme fixing process and the choice of a chitosan in one form rather than another is essentially dictated by criteria of utilisation. In this respect, two forms of chitosan in particular have been used: a chitosan in the form of a fine powder (hereinafter referred to as type I) which, after activation and fixing of the enzyme, gives an enzymatically active product capable of being freeze-dried without any loss of activity. This product is preferably used in suspension with vigorous stirring and is recovered by filtration or centrifuging; a chitosan in the form of flakes which, although fairly rigid, are friable under the effect of mechanical shocks (hereinafter referred to as type II). This chitosan gives a product which does not have any tendency towards sedimentation and which is preferably used for filling columns. The preparation of these two types of chitosan is described in the Examples.

In one preferred embodiment of the process according to the invention, the enzymatically active product is stabilised by eliminating the residual aldehyde groups which have not reacted with the enzyme during fixing. For example, they may be reacted with a suitable chemical compound, for example with a compound containing an amino group. In this respect, it is favourable to use glycine, asparagine and, in particular, lysine, the enzymatically active product thus obtained showing a remarkable affinity for proteic substrates. It is also possible to reduce the residual aldehyde groups, for example with sodium borohydride, which appreciably increases the stability of the enzymatically active product thus treated. These two treatments may of course be combined.

The product obtained by the process according to the invention has an enzymatic activity which approaches that of the corresponding free enzyme, a property which is rarely maintained in known fixing processes. In addition, said product remains stable for several months and has a higher inactivation temperature than the corresponding free enzyme.

As mentioned above, the product may be used for enzymatic reactions instead of the corresponding free enzyme either in suspension (preferably chitosan of type I) or in columns (preferably chitosan of type II). Its use in the food industry would not appear to raise any major difficulty, chitosan being a natural organic substance.

The process according to the invention is illustrated by the following Examples.

EXAMPLE 1

Preparation of chitosan in powder form (type I)

30 g of chitosan are dissolved in dilute acetic acid (700 ml of water and 10 ml of glacial acetic acid) with vigorous stirring until the chitosan is completely dissolved. The viscous solution obtained is filtered through two layers of gauze and then injected in small quantities into two liters of water alkalised to pH 11.0 by the addition of sodium hydroxide. Under these conditions, the chitosan precipitates in the form of fine lightweight particles. Throughout this process, the pH of the solution is kept at its initial value by the addition of sodium hydroxide. After all the chitosan has precipitated, the pH-value of the solution is carefully lowered to 7.5 by the addition of dilute hydrochloric acid. The precipitate collected by centrifuging is washed twice with water and then freeze-dried giving a fine powder of chitosan of type I which is used as such.

FIXING OF TRYPSIN 2.5 g of chitosan of type I are suspended in 50 ml of 0.05 M acetate buffer solution (pH 6.0) over a period of 24 hours. 16.5 ml of 20% glutaraldehyde (obtained by diluting 50% commercial-grade glutaraldehyde with the preceding buffer solution) are then added, followed by stirring for 30 minutes at ambient temperature. After washing with twice-distilled water, the "activated chitosan" is dispersed in 50 ml of 0.1 M borate buffer solution (pH 8.0) containing 0.02 mole/l of $CaCl_2$. This suspension is cooled to 2° C, followed by the addition of 250 mg of trypsin (Merck, crystallised) previously solubilised in 10 ml of 0.001 N HCl and stirring for 2 hours at 2° C. After centrifuging, the product is washed with 50 ml of the following solutions: 0.15 M NaCl solution, 0.1 M borate buffer solution (pH 8.0), and with twice-distilled water (3 times) and then introduced into 50 ml of iced 0.1 M borate buffer solution (pH 8.0) to which 100 mg of solid sodium borohydride are added. After 20 minutes at 2° C, the insoluble enzymatically active product is separated by centrifuging, rewashed with water and preserved in a 0.05 M borate buffer solution (pH 7.5) containing sodium azide as preservative.

The quantity of enzyme fixed to the chitosan by the glutaraldehyde is evaluated by the difference between the quantity added and the quantity present in the residual solution and the washing waters (determination based on UV absorption at 280 nm).

The amidase activity of the product is tested on a synthesis substrate: DL-BAPA (p-nitroanilide of N-benzoyl-DL-arginine) by the method of Erlanger et al, Arch. Biochem. Biophys., 95, 271 (1961), which comprises following the appearance of the p-nitroanilide liberated by enzymatic hydrolysis by measuring its specific absorption at 410 nm. The caseinolytic activity is determined as follows: 4 ml of the above-mentioned borate buffer solution and 1 ml of enzymatic solution containing 300 µg of free trypsin or the equivalent of insolubilised trypsin are added to 5 ml of a substrate consisting of a casein of the Hammarsten type in the form of a 2% solution in a 0.05 M Tris (tris-(hydroxy methyl)-aminomethane) buffer solution (pH 7.5) and heated to 100° C for a period of 15 minutes. After a reaction time of 30 minutes at 35° C, 1 ml of medium is mixed with 3 ml of trichloroacetic acid (3%). After centrifuging, the optical density of the supernatant phase is read off at 280 nm. The caseinolytic activity was arbitrarily selected as being the optical density at 200 nm/mg of protein/30 mn.

The results obtained are as follows:

Of 100 mg of trypsin added to 1 g of chitosan, 92.9 mg of trypsin are fixed. The specific amidase activity (BAPA) - µ moles of p-nitroanilide liberated/mn/mg of enzyme — of the preparation is 49.16% and the specific caseinolytic activity 38.26%.

This product is freeze-dried in the presence of twice its weight of mannitol and the freeze-dried product is preserved for one month. Its enzymatic activity is then measured and found to be the same as that of the fresh product.

EXAMPLE 2

Fixing a protease AP 2.5 g of chitosan (type I) are treated with glutaraldehyde in the same way as described in Example 1. After washing, the product is dispersed in 50 ml of 0.05 M Tris buffer solution (pH 8.0) containing 0.02 mole/liter of $CaCl_2$ and kept at 2° C. This is followed by the addition of 250 mg of commercial-grade protease (protease AP, a product of Societe Suisse Ferments S.A., with subtilo-peptidase activity) in solution in 10 ml of 0.05 M Tris buffer (pH 7.5) containing 0.02 mole/l of $CaCl_2$. After 2 hours' contact with stirring at 2° C, the product is washed with a 0.15 M NaCl solution, then with a 0.05 M Tris buffer solution (pH 8.0) and then with water. Finally, it is taken up in 50 ml of a 0.1 M solution of lysine (pH 8.0) for 15 hours, washed and then treated with sodium borohydride under the same conditions as in Example 1.

The esterase activity of the enzyme is determined on a synthetic substrate: TAME (methyl ester of p-tosyl-L-arginine). 5 ml of TAME (0.025 M in $H_2O$) 1 ml of a 1 M KCl solution and 4 ml of water are introduced into a pH-stat and kept thermostatically at 30° C. The final titration point is fixed at pH 8.0 and adjusted by the addition of a 0.1 N NaOH solution. The reaction is initiated by the addition of protease (0.2 to 1 mg). The consumption of NaOH is recorded. One TAME unit corresponds to the degradation of 1 μ mole of substrate (i.e. 1 μ-equivalent of NaOH) per mn and the specific activity is expressed in TAME units/mg of enzyme. Measurement of the caseinolytic activity is derived from the method of Hagihara et coll., J. Biochem, 45, 185 (1958); 1 ml of an enzymatic solution containing increasing concentrations of free or fixed protease (0 to 180 μg) is added to 1 ml of casein (1.2% in a 0.05 M Tris buffer solution, pH 9.0). After a reaction time of 10 minutes (30° C), the non-hydrolysed casein is precipitated by the addition of 3 ml of a mixture of trichloroacetic acid (0.11 M), sodium acetate (0.22 M), acetic acid (0.33 M). The optical density of the supernatant phase is measured at 275 nm. The specific activity is equal to the optical density at 275 nm/mn/mg of enzyme (determination of the gradient at the beginning of the kinetic curves). Of 100 mg of protease AP added to 1 g of chitosan, 33.7 mg are fixed. In relation to the soluble enzyme, the specific esterase activity is 75.9% (the loss due to the treatment with the borohydride amounts to 3.3%), whilst the caseinolytic activity amounts to 46.15%.

EXAMPLE 3

Fixing of pronase

The procedure of Example 2 is repeated with 250 mg of pronase and without the reduction with sodium borohydride. The caseinolytic activity of the enzymatically active product is measured in the same way as described in Example 2, but with the following modifications: 1 ml of 2% casein in a 0.05 M Tris buffer solution (pH 7.5) and 1 ml of enzymatic solution (free or fixed pronase in different concentrations of from 10 to 160 μg) are incubated for 10 minutes at 40° C. The reaction is terminated by the addition of 3 ml of 5% trichloroacetic acid and the optical density of the supernatant phase is measured at 275 nm.

Of 100 mg of pronase added to 1 g of chitosan, 29 mg are fixed. The caseinolytic activity amounts to 57.60%.

EXAMPLE 4

Preparation of chitosan in flake form (type II)

Chitosan is dissolved in a dilute acetic acid solution (1.8%) so that its concentration in the medium amounts to 2.5% by weight. The solution obtained is filtered through two layers of gauze, after which it is poured onto metal plates (Teflon-treated surface) to form a homogeneous layer (58 ml of solution/100 cm²). The product is dehydrated in an oven at 70° C until a thin film of anhydrous chitosan is formed. The thin film of anhydrous chitosan thus formed is broken up into flakes with an average size of 1 to 2 cm and is used in this form for fixing (type II chitosan).

FIXING A BACTERIAL PROTEASE 5 g of chitosan of type II are dispersed in 150 ml of a 0.1 M borate buffer solution (pH 8.0). After 5 minutes, 15 ml of 25% glutaraldehyde are added and the product left standing for 1 hour at ambient temperature. The product obtained is filtered and, after washing, is suspended in 30 ml of a 0.1 M veronal buffer solution (pH 8.0) containing 0.02 moles/liter of $CaCl_2$ and cooled to 2° C. A concentrated solution of bacterial protease (alkalase Novo, a product of Societe Suisse des Ferments S.A.,) is then introduced (5 ml, 1100 TAME units, i.e. 1.7 g of the commercial product). After standing overnight with gentle stirring at 2° C, the product is separated by filtration, washed with a solution of 0.15 M NaCl, then with a veronal buffer solution and finally with water. Reduction with the borohydride, 1 mg/ml of 0.1 M veronal buffer solution (pH 8.0), is carried out in the same way as described in Example 1.

The esterase activity (TAME) is evaluated in the same way as described in Example 2. The caseinolytic activity is determined as follows: 1 ml of 1% casein in a 0.2 M Tris buffer solution (pH 9.0) and 1 ml of different concentrations of alkalase (10 to 1000 μg) or a known amount of the insoluble product are incubated for 10 minutes at 37° C. 3 ml of 5% trichloroacetic acid are introduced, followed by measurement of the optical density at 280 nm of the supernatant phase. The curve (optical density as a function of concentration) obtained for the free enzyme serves as standard curve.

The insolubilised alkalase is found to contain 41.2 units of TAME/g of dry product, i.e. an equivalent of 66.4 mg of initial alkalase (specific TAME activity: 0.62 U/mg). The caseinolytic activity corresponds to 11 mg of free alkalase/g of dry product. The yield, based on TAME units, amounts to 18.7%.

I claim:

1. A process for the preparation of an enzymatically active product insoluble in aqueous medium, comprising treating chitosan as an insoluble inert support with a dialdehyde to provide an activated chitosan support and thereafter fixing an enzyme containing free amino groups to said activated chitosan support.

2. A process according to claim 1, in which said dialdehyde is glutaraldehyde.

3. A process according to claim 1, in which said chitosan is a powder-form chitosan.

4. A process according to claim 1, in which said chitosan is a flake-form chitosan.

5. A process according to claim 4, in which said chitosan is a flake-form chitosan obtained by fragmenting a film of anhydrous chitosan.

6. A process according to claim 1, in which said enzymatically active product insoluble in aqueous medium is treated with a compound containing an amino group.

7. A process according to claim 1, in which said enzymatically active product insoluble in aqueous medium is treated with a reducing reagent.

8. A process according to claim 1, in which said enzymatically active product insoluble in aqueous medium is treated with a compound containing an amino group and with a reducing reagent.

9. A process according to claim 6, in which said compound containing an amino group is lysine.

10. A process according to claim 7, in which said reducing reactant is sodium borohydride.

11. A process according to claim 8, in which said compound containing an amino group is lysine and said reducing reagent is sodium borohydride.

12. A process according to claim 1, in which said enzymatically active product insoluble in aqueous medium is freeze-dried.

13. A process according to claim 12, in which said enzymatically active product insoluble in aqueous medium is freeze-dried in the presence of twice its weight of mannitol.

14. A process according to claim 1, in which said chitosan and said dialdehyde are reacted at a pH-value from 6 to 8.

15. A process according to claim 1, in which said chitosan and said dialdehyde are reacted at a temperature from 2° to 35° C.

16. A process according to claim 1, in which said enzyme is fixed at a pH-value from 2 to 11.

17. A process according to claim 1, in which said enzyme is fixed at a temperature from 2° C to the temperature at which said enzyme is inactivated.

18. An enzymatically active product insoluble in aqueous medium when prepared by a process as claimed in claim 1.

* * * * *